United States Patent [19]

Watanabe

[11] 4,187,840
[45] Feb. 12, 1980

[54] BONE PLATE CLAMP

[76] Inventor: Robert S. Watanabe, 321 Second St., Suite 1002, Los Angeles, Calif. 90012

[21] Appl. No.: 933,285

[22] Filed: Aug. 14, 1978

[51] Int. Cl.$^2$ .......................... A61B 17/18; A61F 5/04
[52] U.S. Cl. ................................... 128/92 EA; 128/346
[58] Field of Search ............. 128/92 EA, 92 E, 92 D, 128/92 R, 83, 346

[56] References Cited

U.S. PATENT DOCUMENTS

| 2,362,957 | 11/1944 | Hackett | 128/92 EA X |
| 2,427,128 | 9/1947 | Ettinger | 128/92 EA X |
| 3,386,437 | 6/1968 | Treace | 128/92 D |
| 3,477,429 | 11/1969 | Sampson | 128/92 EA |

FOREIGN PATENT DOCUMENTS 574209  10/1977  U.S.S.R. ............... 128/92 EA

OTHER PUBLICATIONS

Orthopaedic Catalogue, Twentieth Edition, Down Bros. & Mayer & Phelps Ltd., London, Toronto, p. G80.
Western S-S Co. (Exhibits A-E), bone clamp, submitted Sep. 29, 1979 as prior art.

Primary Examiner—Ronald L. Frinks
Attorney, Agent, or Firm—Donald D. Mon

[57] ABSTRACT

A bone plate clamp for attachment to a bone. The clamp includes a base member with a guideway and an abutment face. A jaw member has a pair of jaw faces which face the abutment face. The jaw member is slidably mounted to the base member at the guideway and is moveable toward and away from the abutment face by a leadscrew that is threaded to the base member. A coupler joins the leadscrew to the jaw member. A handle is provided on the base member. The leadscrew has a grip with a first and a second diameter to provide for different rates of movement of the jaw member.

8 Claims, 4 Drawing Figures

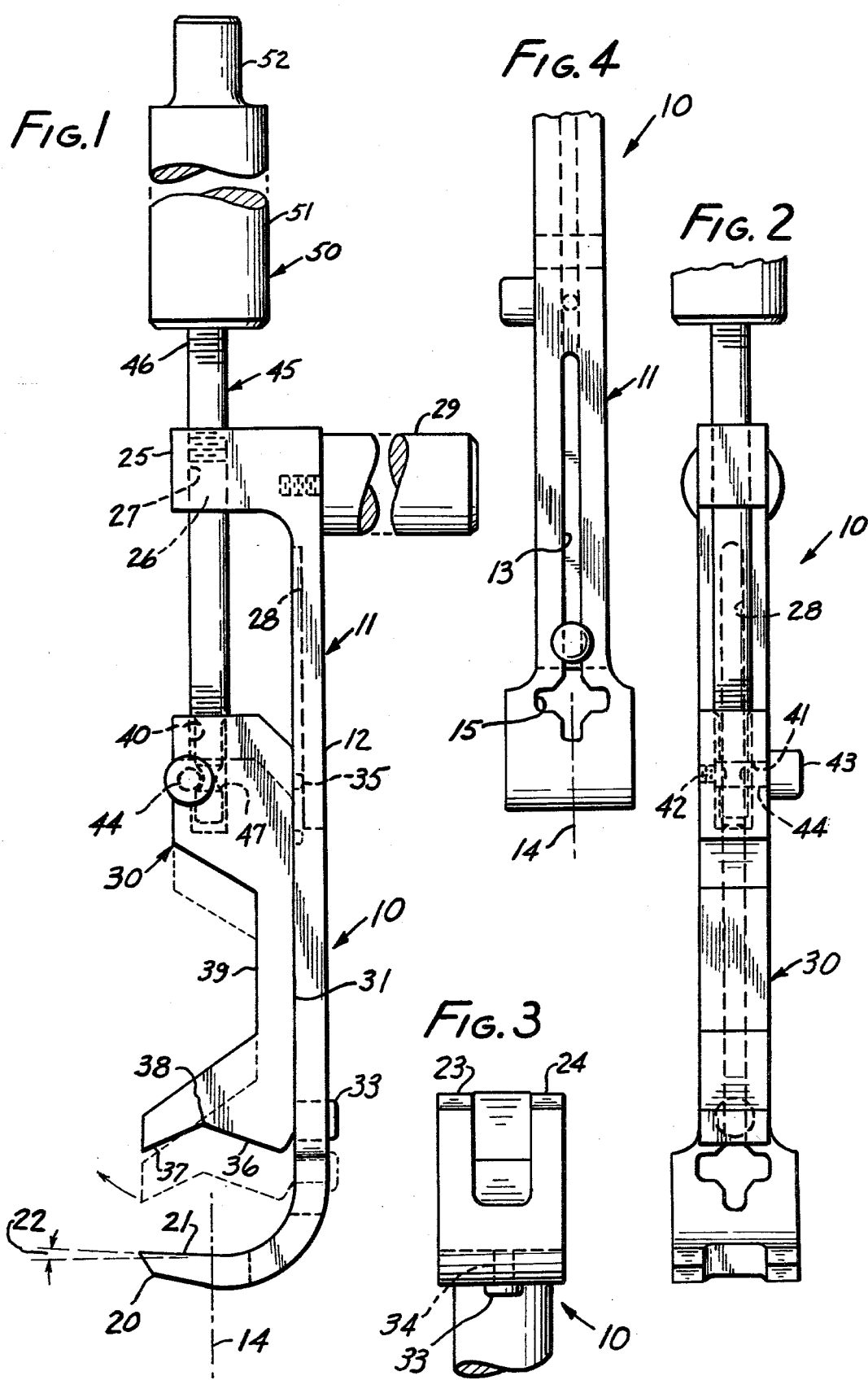

BONE PLATE CLAMP

This invention relates to a bone plate clamp.

Bone plate clamps are used to reduce bone fractures and to hold the bone in adjusted and aligned position while a bone plate or a bone nail is installed. Examples of such techniques are the application of a plate to lend strength to a broken bone, or to hold the bone aligned while a bone nail is being driven or a replacement femur is being applied.

It is a matter of general knowledge that persons with fractures or other conditions which require the use of plates or nails are usually in such an injured, aged, or otherwise debilitated condition, that surgery itself constitutes a substantial risk of life. Furthermore, especially with the aged, the prognosis darkens with extension of time under anesthetic on the operating table. Reduction of operating time under anesthesia of even a few minutes dramatically improves the likelihood of survival. Therefore to an orthopedist, speed in the operation is a prime objective, and anything which can reduce the time required for a procedure is likely to be of profound benefit to the patient.

However, the orthopedist must work in locations where it is difficult to see the existing situation without taking substantial time in the process. This is because fractures are often located on the distal side of the bone from the surgeon and located within an opening formed only by the surgeon's knife which should of course be minimized. Also, critical blood vessels are frequently located in close proximity to the operating field and if damaged they must be repaired. This is another time consuming activity. The bone clamp must be of a structure which occupies minimal envelope size and is without protrusions which could damage tissue and blood vessels.

In addition, surgical clamps must be sterile. In order to be sterilized they must be subject to disassembly. Some prior art clamps, in providing a disassembling function, do so in such a way that they come apart during the operating procedure unless special care is taken to avoid this event. The surgeon already has far too many problems without adding to it a concern for manipulating his instrument so that it does not fall apart in use.

Furthermore, a surgeon cannot be expected to optimal work of exquisite fine-ness while manipulating heavy devices. Lightening the weight of a clamp is another important objective.

The clamp according to this invention is light-weight, reliable in use, and readily disassembleable but structurely reliable in use. It is costructed so that it can reach into obscure regions with minimal risk, and is provided with features which enable the surgeon to speed up his procedure.

A bone plate clamp according to this invention includes a base member with a guideway having an axis. An abutment member is carried by the base plate and has an abutment face. A jaw member is slidably fitted to the base plate at said guideway for axial movement along the axis, and it carries a first jaw face and a second jaw face, both of which face the abutment face, and which form an obtuse angle with one another. The abutment face makes an acute angle with the axis. An internal thread in a passage through the base member mounts a leadscrew parallel to the axis. The leadscrew is rotatably engaged to the thread and projects from both ends of the passage. Releasable coupler means couples the leadscrew to the jaw member for relative rotation and simultaneous axial movement. Grip means on the leadscrew has a relatively larger diameter section and a relatively smaller diameter section, both exposed so as to be engageable by the hand for driving the screw at different rates of speed. A handle is attached to the base member which extends laterally therefrom on a side opposite from the jaw member.

According to a preferred but optional feature of the invention, the first and second jaw faces meet at an apex. The second jaw face is farther from the guideway than the first jaw face and it extends a lesser lateral distance than the first jaw face.

According to still another preferred but optional feature of the invention, the coupler means comprises a transverse member and a peripheral groove in the leadscrew. The transverse member and the leadscrew are insertable in the jaw member, whereby the transverse pin prevents escape of the leadscrew.

According to yet another preferred but optional feature of the invention, the guideway comprises an axial slot, and the jaw member carries a retention pin having a head with greater lateral dimensions than the slot. The slot has an entrance portion with a lateral dimension greater than that of the head to enable the jaw member to be mounted to and removed from the guideway when the retention member is aligned with said entrance portion.

The above and other features of this invention will be fully understood from the following detailed description and the accompanying drawings, in which:

FIG. 1 is a side elevation of the presently preferred embodiment of the invention;

FIG. 2 is a left-hand view in FIG. 1;

FIG. 3 is a bottom view in FIG. 1;

FIG. 4 is a fragmentary right-hand view of FIG. 1.

In FIG. 1 a bone plate clamp 10 is shown which includes a base member 11. The base member in side view is generally U-shaped and in its central portion 12 it has a guideway 13 in the form of a slot which extends entirely through the central portion and extends parallel to an axis 14. At one end of the guideway there is provided an enlarged entrant portion 15 with greater lateral dimensions than the remainder of the slot for a purpose yet to be described.

At the same end there is provided an abutment member 20 which comprises a shoulder having an abutment face 21 thereon. This face makes an acute angle 22 (about 5°) with the normal to axis 14 on the same side as the second shoulder, and therefore it makes an acute angle with the axis. As best shown in FIG. 3 it is preferably bifurcated, having a pair of fingers 23, 24. The abutment faces may be provided with striations or a roughened finish to give a better grip if desired.

The base member also includes a second shoulder 25 with a passage 26 therethrough. This passage has an internal thread 27. A stabilizer groove 28 extends along the central portion of the base member. A handle 29 is threadedly attached to the base member on the other side from the second shoulder 25.

A jaw member 30 is slidably fitted to the base member for axial movement along the same. It has a flat bottom 31 from which there projects a retention pin 32. The retention pin has a head 33 with lateral dimensions greater than the width of the guideway slot, and a stem 34 with lateral dimensions not greater than the width of the slot. The lateral dimensions of the head are not greater than those of the entrant portion 15 so that the jaw member can be attached to the base member by passing the head through the entrant portion and then sliding the jaw member away therefrom so that the jaw member will be slidably held to the base member. A stabilizer pin 35 with lateral dimensions not greater than those of stabilizer groove 28 rides in the stabilizer groove, whereby it and the retention pin provide lateral stability to the jaw member.

The jaw member includes a first and a second jaw face 36, 37 respectively. These are preferably planar and intersect at the apex 38 of an obtuse angle (about 150°–165°). Each makes an acute angle with the axis and forms a substantially equal angle with the normal to said axis. The lateral dimensions of the second face 37 (the farther of the faces from the base member) is shorter than that of the first jaw face 36. A trough 39 is formed in the jaw member to lighten its weight, because this portion is not needed for strength of the clamp.

A bearing recess 40 is formed in the jaw member facing the second shoulder. A transverse passage 41 is formed which partly intersects recess 40 and has a thread 42 at one end. A coupler 43 comprises a transverse member 44 which passes through transverse passage 41 and is threaded into thread 42. It has a cylindrical outer boundary which projects into bearing recess 40.

The purpose of coupler 43 is to couple a leadscrew 45 to the jaw member. The leadscrew has a thread 46 which threadedly engages internal thread 27 in the second shoulder. Therefore turning the leadscrew will move the leadscrew axially relative to the base member. The leadscrew includes a peripheral groove 47 which is engaged by the transverse member so as to couple the jaw member and the leadscrew together for relative rotation and simultaneous axial movement.

Grip means 50 is integral with the leadscrew and has a relatively larger diameter section 51 and a relatively smaller diameter section 52. These are striated or knurled to give the surgeon a good grip. It is evident that the leadscrew can be driven faster by manipulating the smaller grip means than the larger grip means.

The operation of the bone clamp should be evident from the foregoing. When it is to be disassembled it is moved to the position shown in dashed line in FIG. 1. The transverse member 44 is unthreaded. The leadscrew is backed out of bearing recess 40, and the jaw member is removed from the base member. Reassembly is the reverse of the foregoing.

To stabilize the structure, the jaw member is retracted so the retention pin is away from the entrant portion 15. The entrant portion 15 is located where the retention pin is unlikely to reach during normal operative procedures on bones of the size on which the clamp will be used.

Thereafter the device can simply be used very much as a wrench is used.

It will be noted that the structure is readily disassembleable for sterilizing. It is built so that it cannot come apart in normal operative procedures, and the size and the construction of the faces is such that the overhang of the jaw relative to the bone is minimized. In use, it is customary for the abutment member to be placed over the bone and a plate put between such of the sets of faces as is appropriate. Then the leadscrew is turned to tighten down the jaw face and to hold the assembly while nails are being driven.

This device is therefore elegantly simple and rugged and reliable in use.

This invention is not to be limited by the embodiment shown in the drawings and described in the description which is given by way of example and not of limitation, but only in accordance with the scope of the appended claims.

I claim:

1. A bone plate clamp comprising: a base member; a guideway on said base member having an axis; an abutment member carried by said base plate; an abutment face on said abutment member; a jaw member slidably fitted to said base member by said guideway for axial movement along said axis; a first jaw face and a second jaw face on said jaw member, both of said jaw faces facing said abutment face, said jaw faces making an obtuse angle with one another, and the abutment face making an acute angle with the normal to said axis; an internal thread in a passage through said base member, parallel to said axis; a leadscrew rotatably engaged to said thread and projecting from said base member at each end of said passage; releasable coupler means coupling the leadscrew to the jaw member for relative rotational movement and simultaneous axial movement; grip means on said leadscrew, said grip means having a relatively larger diameter section and a relatively smaller diameter section, both exposed to be engageable by the hand; and a handle attached to the base member extending laterally therefrom on a side opposite from the jaw member.

2. A bone plate clamp according to claim 1 in which the first and second jaw faces meet at an apex, the second jaw face being farther from the guideway than the first jaw face, and extending a lesser lateral distance than the first jaw face, said jaw faces forming a substantially equal angle with a normal to said axis.

3. A bone plate clamp according to claim 1 in which the coupler means comprises a transverse member and the leadscrew bears a peripheral groove said transverse member and leadscrew being insertable in said jaw member, whereby the transverse member prevents escape of the lead screw.

4. A bone plate clamp according to claim 3 in which the transverse member is threadably removably attachable to the jaw member.

5. A bone plate clamp according to claim 1 in which the guideway comprises an axial slot, and the jaw member carries a retention pin having a head with greater lateral dimension than the slot, and in which the slot has an entrant portion with lateral dimensions greater than those of the head to enable the jaw member to be mounted to and removed from said guideway when the retention member is aligned with said entrant portion.

6. A bone plate clamp according to claim 5 in which a stabilizer pin projects from the jaw member, and in which a stabilizer groove extends axially along the body member and receives and stabilizes the jaw member as it moves axially.

7. A bone plate clamp according to claim 1 in which the jaw member is relieved along its edge away from the guideway to lighten the clamp.

8. A bone plate clamp according to claim 1 in which the abutment member is bifurcated.

* * * * *